United States Patent [19]

Fogarty

[11] 4,403,612
[45] Sep. 13, 1983

[54] DILATATION METHOD

[76] Inventor: Thomas J. Fogarty, 770 Welch Rd., Palo Alto, Calif. 94304

[21] Appl. No.: 362,295

[22] Filed: Mar. 26, 1982

Related U.S. Application Data

[62] Division of Ser. No. 198,342, Oct. 20, 1980, Pat. No. 4,338,942.

[51] Int. Cl.³ .......................................... A61M 29/02
[52] U.S. Cl. .................................. 128/344; 128/325; 128/348.1
[58] Field of Search ..................... 128/344, 325, 348.1, 128/207.15; 604/101, 96

[56] References Cited

U.S. PATENT DOCUMENTS

| | | | |
|---|---|---|---|
| 2,616,429 | 11/1952 | Merenlender | 604/105 |
| 2,688,329 | 9/1954 | Wallace | 604/95 |
| 3,426,744 | 2/1969 | Ball | 604/96 X |
| 3,481,339 | 12/1969 | Puig | 128/207.15 |
| 3,799,172 | 3/1974 | Szpur | 604/105 |
| 3,837,347 | 9/1974 | Tower | 128/785 |
| 3,996,938 | 12/1976 | Clark | 128/348.1 |
| 4,046,151 | 9/1977 | Rose | 604/21 X |
| 4,105,022 | 8/1978 | Antoshkiw et al. | 128/713 |
| 4,261,339 | 4/1981 | Hanson et al. | 128/344 X |

FOREIGN PATENT DOCUMENTS 512456  9/1939  United Kingdom ................ 128/344

*Primary Examiner*—Michael H. Thaler
*Attorney, Agent, or Firm*—Naylor, Neal & Uilkema

[57] ABSTRACT

A dilatation catheter is provided with a double lumen tube and inner and outer inflatable and deflatable balloon elements, one within the other. The inner bag element is twisted for retraction while the outer bag element is inflated. Subsequent deflation of the outer bag element serves to further laterally compress the inner bag element and provide a smooth buffering surface for engagement with blood vessel walls as the catheter is moved past them.

4 Claims, 7 Drawing Figures

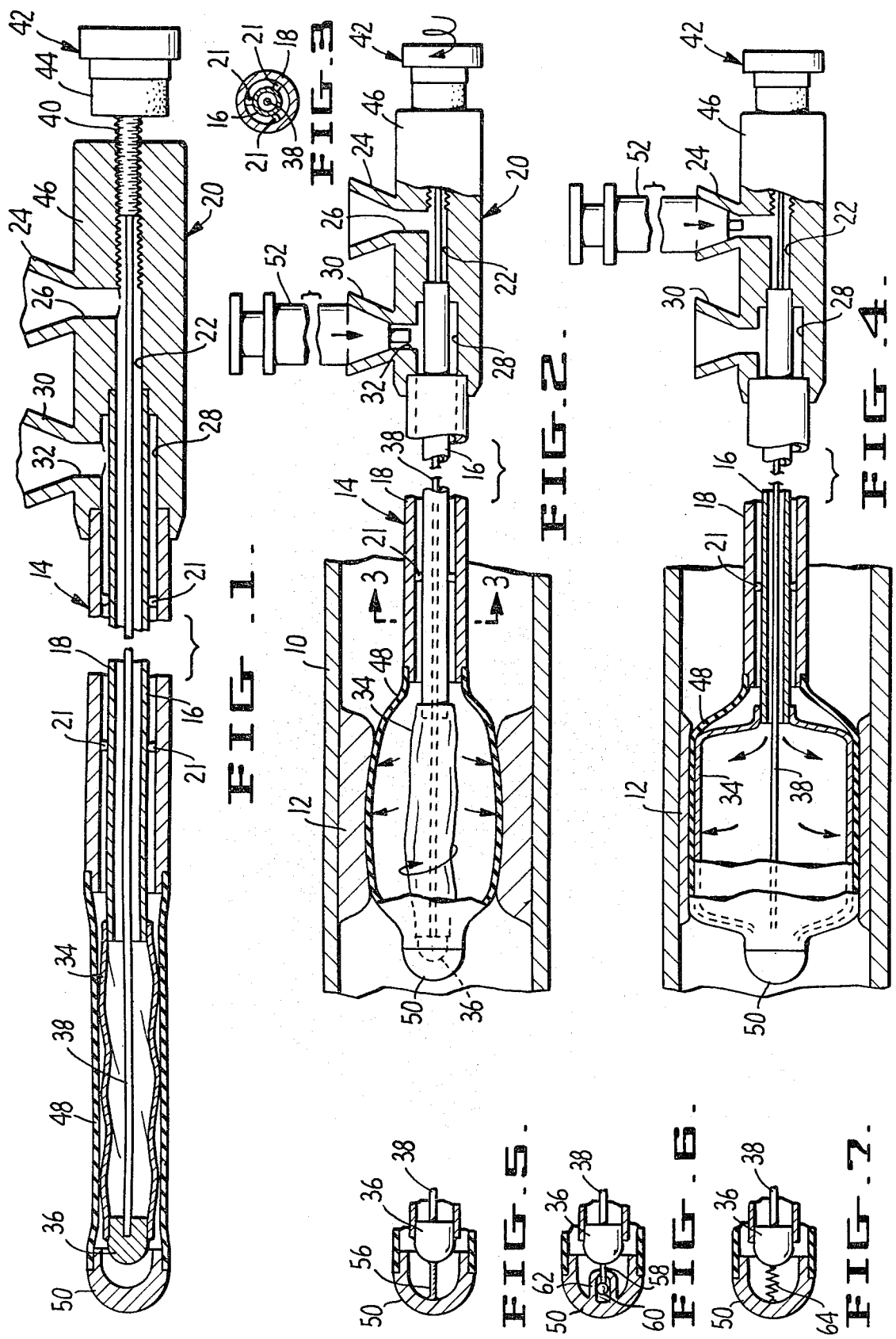

DILATATION METHOD

This application is a division, of application Ser. No. 198,342, filed Oct. 20, 1980, now U.S. Pat. No. 4,338,942.

RELATED APPLICATION

The dilatation catheter apparatus and method of the subject application is an improvement upon the catheter apparatus and method shown and described in my co-pending application, Ser. No. 116,816, filed Jan. 30, 1980 for DILATATION CATHETER APPARATUS AND METHOD.

BACKGROUND OF THE INVENTION

The inventive concept of the invention of my above-identified co-pending application is to achieve dilatation by inflating a catheter-carried balloon element of large diameter and to achieve ready placeability and removability of the balloon element through axial twisting of the deflated balloon element to decrease its transverse dimension.

SUMMARY OF THE INVENTION

The improvement of the present invention over that of my co-pending application consists of the combination with the latter of a first means to enclose the twisted non-inflated balloon element and prevent if from rubbing against the wall of the artery or vein during insertion and removal of the catheter and second means to hold the wall of the artery or vein away from the balloon element so that said wall does not tend to be disturbed by the twisting or untwisting of the balloon element.

In the preferred embodiment of the invention the first and second means are provided in the form of an outer second balloon element which is elastic in nature and independently inflatable. The second balloon element in its deflated condition provides a smooth surface for engaging the artery or vein and in an inflated condition holds the artery or vein away from the inner balloon while the latter is either twisted or untwisted.

DESCRIPTION OF THE DRAWING

FIG. 1 is a view in section of the catheter.

FIG. 2 is a view partly in elevation and partly in section showing the catheter emplaced in an occluded artery.

FIG. 3 is a view taken along lines 3—3 of FIG. 2.

FIG. 4 is a view similar to that of FIG. 2 but showing the instrument in full dilatation condition.

FIG. 5 is a view partly in section and partly in elevation showing one form of connection that may be employed between the tips of the inner and outer catheters.

FIG. 6 is a view like that of FIG. 5 showing another form of connection between the catheter ends.

FIG. 7 is a view like that of FIG. 5 showing still a further form of connection between the catheter ends.

DESCRIPTION OF THE PREFERRED EMBODIMENT

FIG. 2 illustrates a blood vessel 10 which is partially occluded by an extended occlusion 12. As shown, the vessel takes the form of an artery and the occlusion is what is commonly known as an arteriosclerotic plaque or atheroma. This is the type of adhering occlusion with which the subject apparatus and method is expected to find primary application. It should be understood, however, that the inventions are applicable in treating other types of occluded vessels where dilatation is desired. For example, the inventions may be used in treating occlusions resulting from fibromuscular displasia in veins.

The catheter 14 comprises inner and outer concentric flexible plastic tubes 16 and 18, the inner tube being supported on projections 21 which are carried by and extend inwardly from outer tube 18. The proximal end of tube 16 is attached to a fitting 20 so that the interior of the tube is in communication with passageway 22. A syringe receptor socket 24 is provided with a passageway 26 which is in communication with passageway 22. The proximal end of tube 18 is attached to fitting 20 so that the interior of the tube is in communication with passageway 28. A syringe receptor socket 30 is provided with a passageway 32 which connects with passageway 28.

An inflatable bag 34 has one end thereof bonded to tube 16 and has the other end thereof bonded to tip member 36. Member 36 has fixedly attached thereto guide wire 38. The proximal end of guide wire 38 is fixedly attached to the threaded stem 40 of control knob 42. A sealing disc 44 is carried by control knob 42. Fitting 30 is provided with internal threads 46 with which stem 40 is threadably engaged.

A second balloon element or inflatable bag 48 has its proximal end bonded to the distal end of tube 18. The other end of balloon element 48 is bonded to catheter tip member 50.

The inner balloon element 34 is preferably made of flexible non-elastic material, such as vinyl plastic. The outer balloon element 48 is made of a flexible elastic material, such as latex.

The catheter is used in the following manner. It is first brought to the condition shown in FIG. 1 in which the knob 42 has been rotatably backed off from the fitting 20 to twist, shorten, laterally compress and rigidify the inner balloon element 34. The catheter is then introduced into the vessel 10 through an incision, not shown.

When the catheter has been properly emplaced relative to the atheroma 12, as shown in FIG. 2, the outer balloon element 48 is inflated by applying syringe 52 to receptor 30 and introducing an incompressible fluid into balloon element 48 along passageway 28 and the annular space between the tubes 16 and 18. While the outer balloon element is maintained in an inflated condition, the inner balloon element 34 is untwisted by rotating knob 42 to move the sealing disc 44 into engagement with the fitting. The syringe 52 is then operated to remove the fluid from the outer balloon and thereby deflate the outer balloon.

The syringe is then fitted to receptor 24 and the incompressible fluid is passed through passageway 22 and the interior of tube 16 to inflate the inner balloon element 34. This causes the expansion of the outer balloon element 48 and results in the catheter condition illustrated in FIG. 4 wherein the atheroma 12 is being compressed by the inflated inner bag and the non-inflated but expanded outer bag. Once the atheroma has been adequately compressed, the catheter is prepared for retraction from the artery as follows. The syringe is used to remove the fluid from the inner balloon element 34, thereby deflating this element. The syringe is then switched to receptor 30 and the outer balloon element 48 is inflated and maintained in inflated condition while the knob 42 is backed away from the fitting 20 to twist balloon element 34 into a laterally retracted, somewhat shortened, and stiffened condition. The outer balloon element is then deflated. The catheter is now in the condition of FIG. 1 for movement to a new section of artheroma to be treated or for withdrawal from the vessel 10.

It will be appreciated that twisting and untwisting of the inner balloon element takes place while the outer balloon element is inflated and out of contact with the inner balloon element. Thus the tissue of the artheroma is not exposed to the twisting or untwisting of the inner balloon element. This means that the production of potential embolism material is minimized. Furthermore, since the outer balloon element is not in engagement with the inner balloon element when the latter is subjected to a twisting or untwisting action there is no tendency for the outer balloon element to twist in one way or the other in response to movement of the inner balloon element. When the outer balloon element is subsequently deflated to the FIG. 1 condition it presents a substantially smooth untwisted surface in contact with the artery wall during positional emplacement of the catheter.

It may be desirable to provide a connection means between the tip members 36 and 50 so as to tend to maintain them concentric to each other when the inner balloon element 34 is being retracted by twisting or to give some additional support to tip member 50. This may be accomplished in several ways, some of which are shown in FIGS. 5–7. In FIG. 5 a cord tie 56 is connected at its ends to the tip members 36 and 50. In FIG. 6 the connection means comprises a rod and ball element 58, 60 carried by inner tip member, ball 60 being slidably disposed in captive relation in a socket member 62 carried by the outer tip member 50. In FIG. 7 the connection means comprises a spring 64, the ends of which are attached to tip members 36 and 50.

What is claimed is:

1. A method for inserting an inflatable balloon into a partially occluded section of a blood vessel and for dilating said section comprising axially twisting the balloon to reduce its diameter for passage along said vessel and into said partially occluded section, moving said balloon along said vessel while maintaining its axially twisted condition to emplace it in said section, moving said occluded section away from said balloon so that said section is not in pressing relationship with respect to said balloon and holding said section in such position while axially untwisting said balloon to an untwisted condition, and inflating said balloon to dilate said section.

2. The method of claim 1, further comprising the steps of subsequently deflating said balloon, moving said occluded section away from said balloon so that said section is not in pressing relationship with respect to said balloon and holding said section in such position while axially twisting said balloon to reduce its diameter for passage along said vessel, and withdrawing said balloon from said vessel.

3. A method for inserting an inflatable first balloon into a partially occluded section of a blood vessel and for dilating said section comprising laterally enclosing said first balloon within a non-twistable, elastic, inflatable, second balloon, axially twisting the first balloon to reduce its diameter for passage along said vessel and into said partially occluded section, moving said balloons along said vessel while maintaining the axially twisted condition of said first balloon to emplace them in said section, inflating said second balloon to maintain said occluded section and said second balloon is spaced apart relation to said first balloon while axially untwisting said first balloon, deflating said second balloon, and inflating said first balloon to expand said second balloon and dilate said second section.

4. The method of claim 3, further comprising the steps of subsequently deflating said first balloon, inflating said second balloon to maintain said occluded section and said second balloon in spaced apart relation to said first balloon while axially twisting said first balloon to reduce its diameter for passage along said vessel, deflating said second balloon, and withdrawing said balloons from said vessel.

* * * * *